(12) United States Patent
Tsumatori

(10) Patent No.: US 11,937,898 B2
(45) Date of Patent: Mar. 26, 2024

(54) TIME INTENSITY CURVE MEASURING APPARATUS

(71) Applicant: Shimadzu Corporation, Kyoto (JP)

(72) Inventor: Hiroyuki Tsumatori, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 245 days.

(21) Appl. No.: 15/889,570

(22) Filed: Feb. 6, 2018

(65) Prior Publication Data

US 2018/0220894 A1 Aug. 9, 2018

(30) Foreign Application Priority Data

Feb. 7, 2017 (JP) ................................ 2017-020111

(51) Int. Cl.
*A61B 5/00* (2006.01)
*G06T 7/00* (2017.01)
(Continued)

(52) U.S. Cl.
CPC .......... *A61B 5/0071* (2013.01); *A61B 5/0035* (2013.01); *A61B 5/0044* (2013.01);
(Continued)

(58) Field of Classification Search
CPC ... A61B 5/0071; A61B 5/0035; A61B 5/0044; A61B 5/0077; A61B 5/7203;
(Continued)

(56) References Cited

U.S. PATENT DOCUMENTS

2009/0116715 A1* 5/2009 Bredno ................. A61B 6/527
  382/130
2011/0152692 A1* 6/2011 Nie ...................... A61B 5/0077
  600/473

(Continued)

FOREIGN PATENT DOCUMENTS

CN   101448457 A   6/2009
CN   105074433 A   11/2015
(Continued)

OTHER PUBLICATIONS

Glatz J, Symvoulidis P, Garcia-Allende PB, Ntziachristos V. Robust overlay schemes for the fusion of fluorescence and color channels in biological imaging. J Biomed Opt. Apr. 2014;19(4):040501. doi: 10.1117/1.JBO.19.4.040501. PMID: 24695844. (Year: 2014).*

(Continued)

*Primary Examiner* — Christopher Koharski
*Assistant Examiner* — Richmond J Van Winter
(74) *Attorney, Agent, or Firm* — Maier & Maier, PLLC

(57) ABSTRACT

An image processing unit includes a grayscale image creating unit, a shininess region removal unit, a region of interest tracing unit, and a time intensity curve measuring unit. The time intensity curve measuring unit includes a pixel value measuring unit which measures the pixel value of a specific point in the fluorescence image photographed by the fluorescence image pickup element, and a measurement position movement unit which moves the measurement position of the pixel value in the pixel value measuring (Continued)

unit in accordance with the region of interest traced by the region of interest tracing unit.

4 Claims, 18 Drawing Sheets

(51) Int. Cl.
 *A61B 90/00* (2016.01)
 *G16H 30/40* (2018.01)
(52) U.S. Cl.
 CPC .......... *A61B 5/0077* (2013.01); *A61B 5/7203* (2013.01); *G06T 5/70* (2024.01); *G06T 7/0016* (2013.01); *A61B 2562/0233* (2013.01); *A61B 2576/023* (2013.01); *G06T 2207/10016* (2013.01); *G06T 2207/10024* (2013.01); *G06T 2207/10048* (2013.01); *G06T 2207/10064* (2013.01); *G06T 2207/20182* (2013.01); *G06T 2207/30048* (2013.01); *G06T 2207/30096* (2013.01); *G06T 2207/30101* (2013.01)
(58) Field of Classification Search
 CPC ...... A61B 2562/0233; A61B 2576/023; A61B 90/361; A61B 90/37; A61B 5/0033; A61B 2090/373; A61B 2576/00; A61B 6/527; G06T 5/002; G06T 7/0016; G06T 2207/10016; G06T 2207/10024; G06T 2207/10048; G06T 2207/10064; G06T 2207/20182; G06T 2207/30048; G06T 2207/30096; G06T 2207/30101; G16H 30/40
 See application file for complete search history.

(56) References Cited

U.S. PATENT DOCUMENTS

| | | | |
|---|---|---|---|
| 2012/0220840 A1* | 8/2012 | Morita | A61B 1/0638 600/109 |
| 2015/0256760 A1 | 9/2015 | Ju et al. | |
| 2016/0041098 A1* | 2/2016 | Hirawake | A61B 1/0655 250/206 |
| 2016/0262638 A1* | 9/2016 | Kamada | A61B 5/0263 |
| 2016/0314585 A1* | 10/2016 | Thomas | G06V 40/10 |
| 2016/0377545 A1* | 12/2016 | Wang | G06F 3/04886 250/459.1 |
| 2017/0084012 A1* | 3/2017 | Walle-Jensen | G16H 30/20 |
| 2017/0084024 A1* | 3/2017 | Gurevich | A61B 5/7239 |
| 2017/0280029 A1* | 9/2017 | Steiner | A61B 1/0005 |
| 2017/0360275 A1* | 12/2017 | Yoshizaki | A61B 1/00055 |
| 2018/0042481 A1* | 2/2018 | Tian | H04N 23/56 |
| 2018/0220052 A1* | 8/2018 | Granneman | H04N 23/73 |
| 2019/0122345 A1* | 4/2019 | Kamio | G06V 10/143 |
| 2021/0217172 A1* | 7/2021 | Oshima | G06T 7/20 |

FOREIGN PATENT DOCUMENTS

| | | | | |
|---|---|---|---|---|
| CN | 105705084 A | | 6/2016 | |
| JP | 2009-538171 A | | 11/2009 | |
| WO | WO-2009092162 A1 | * | 7/2009 | ........... A61B 5/0059 |
| WO | WO-2016039002 A1 | * | 3/2016 | ............ A61B 10/00 |

OTHER PUBLICATIONS

Chinese Office Action dated May 15, 2020, in connection with corresponding CN Application No. 201810122813.6 (17 pgs., including machine-generated English translation).

* cited by examiner

TIME INTENSITY CURVE MEASURING APPARATUS

FIELD

The invention relates to a time intensity curve measuring apparatus which measures a time intensity curve illustrating a temporal change in pixel value of light emission from a fluorescent dye administered into a body of a subject.

BACKGROUND

A technique called near-infrared fluorescence imaging is used for contrast of blood vessels or lymph ducts in surgical operations. In the near-infrared fluorescence imaging, by injecting indocyanine green (ICG) which is a fluorescent dye into the body of the subject by an injector or the like, the indocyanine green is administered to the affected part. When the indocyanine green is irradiated with near-infrared rays having a wavelength of about 600 to 850 nm (nanometers) as excitation ray, indocyanine green emits near-infrared fluorescence with a wavelength of about 750 to 900 nm. The fluorescence is photographed by an image pickup element capable of detecting near-infrared rays and the image is displayed on a display unit such as a liquid crystal display panel. According to the near-infrared fluorescence imaging, it is possible to observe blood vessels, lymph ducts, and the like existing at a depth of about 20 mm from the body surface.

Further, in recent years, a method of fluorescently labeling a tumor and using the same for surgical navigation has attracted attention. 5-aminolevulinic acid (5-ALA) is used as a fluorescent labeling agent for fluorescently labeling the tumor. When 5-aminolevulinic acid (hereinafter abbreviated as "5-ALA") is administered to a subject, 5-ALA is metabolized to protoporphyrin IX (protoporphyrin nine/PpIX) which is a fluorescent dye. Further, PpIX accumulates specifically in cancer cells. When visible rays having a wavelength of about 410 nm are irradiated toward PpIX which is a metabolite of 5-ALA, red visible rays having a wavelength of about 630 nm are emitted as fluorescence from PpIX. The fluorescence from the PpIX is photographed with the image pickup element and observed, thereby making it possible to check the cancer cells.

In such an imaging apparatus that photographs fluorescence from a fluorescent dye intruded into the body, analysis of a time intensity curve (TIC) that draws a signal change curve of a time-direction of the fluorescence intensity of the region of interest is performed, and by obtaining the time until the pixel value of the region of interest (ROI) becomes a peak, it is possible to quantitatively evaluate the contrast time of the fluorescent dye such as indocyanine green. In such a case, it is necessary to trace the moving region of interest over time.

In order to obtain such a time intensity curve, it is necessary to set the region of the blood vessel of the subject as a region of interest and to measure the pixel value of the near-infrared image of the region of interest over time. On the other hand, the region of interest of the subject moves due to body movement etc. of the subject. For this reason, in order to measure an accurate time intensity curve, it is necessary to trace the region of interest corresponding to the body movement or the like of the subject.

Patent Literature 1 discloses a photographing apparatus that recognizes the movement of a blood vessel using a pair of markers.

[Patent Literature 1] JP-T-2009-538171

SUMMARY

In the method described in Patent Literature 1, it is necessary to place a marker in place. For this reason, it is necessary to perform a special treatment for placing the marker in the body of the subject. In addition, the part in which the marker can be placed is limited, and it is not possible to execute tracing the region of interest for the part in which it is difficult to place the marker.

The invention has been made in order to solve the above problems, and an object of the invention is to provide a time intensity curve measuring apparatus capable of accurately obtaining a time intensity curve without using a marker.

According to the invention, there is provided a time intensity curve measuring apparatus which measures a time intensity curve illustrating a temporal change in pixel value of light emission from a fluorescent dye administered into a body of a subject, the apparatus including: an excitation ray source which emits excitation ray for exciting a fluorescent dye administered into the body of the subject toward the subject; an image pickup unit which photographs a fluorescence image from the fluorescent dye and a color image including a tissue of the subject; a region of interest tracing unit which traces a region of interest on the basis of the color image photographed by the image pickup unit; a pixel value measuring unit which measures a pixel value of a preset measuring point in the fluorescence image photographed by the image pickup unit; and a measurement position movement unit which moves the measurement position of a pixel value in the pixel value measuring unit in association with the region of interest traced by the region of interest tracing unit.

Here, the term "tissue" means a tissue such as an organ, which is a visceral organ of a subject. Further, the "tissue" includes tissues other than organs such as skin to be transplanted at the time of skin transplantation. In the specification and the like of this application, various tissues including organs in a subject are simply referred to as "tissue".

According to the invention, the image pickup unit includes a first photographing element which photographs a fluorescence image from the fluorescent dye, and a second photographing element which photographs a color image including the tissue of the subject.

According to the invention, the apparatus further includes: a shininess region removal unit which removes a shininess region on a tissue surface on the basis of a color image including the tissue, in which the grayscale image creating unit creates a grayscale image on the basis of the color image after the shininess region is removed by the shininess region removal unit.

According to the invention, by tracing the region of interest on the basis of the color image, even when the region of interest moves due to body movement or the like of the subject, it is possible to always maintain the pixel value of the constant position. Therefore, it is possible to obtain an accurate time intensity curve.

According to the invention, since the region of interest is traced on the basis of the image after the shininess region is removed, the region of interest can be more accurately traced.

DETAILED DESCRIPTION OF THE DRAWINGS

Figure 1:
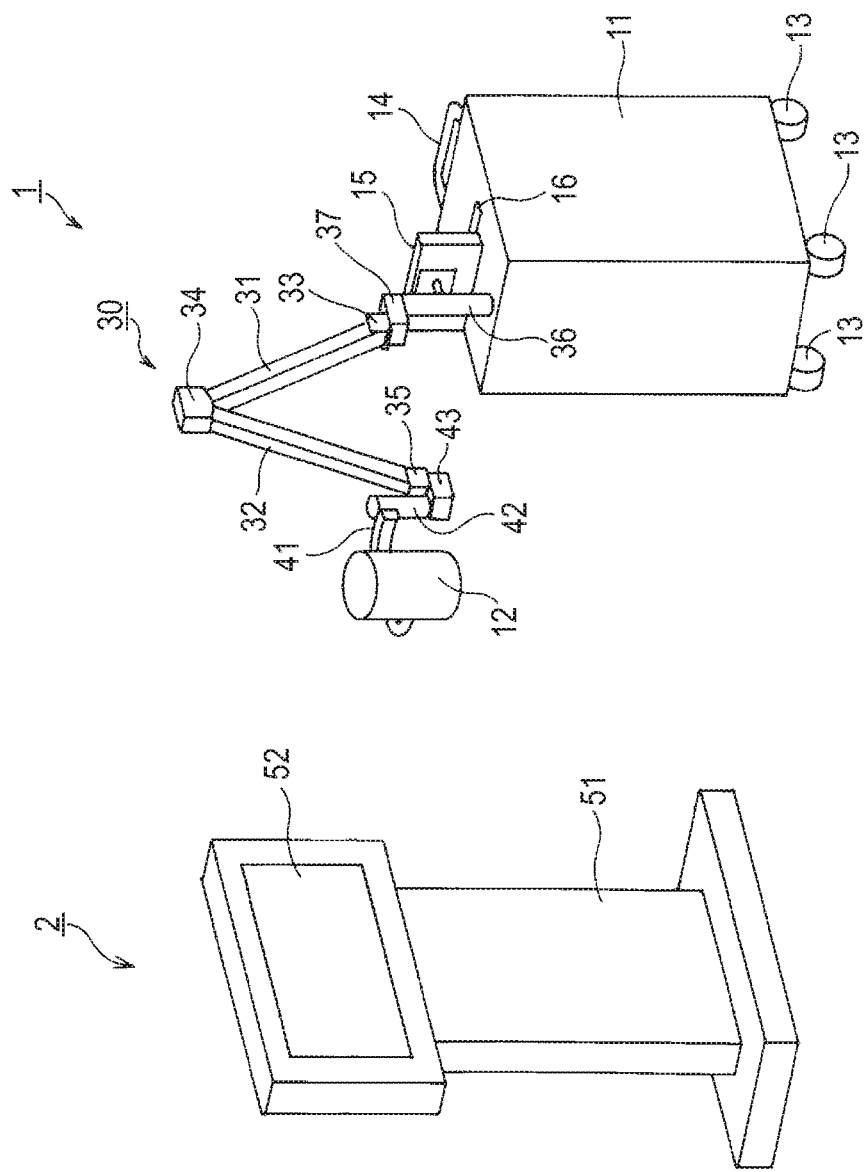
FIG. 1 is a perspective view illustrating an imaging apparatus 1 equipped with a region of interest tracing apparatus according to the invention, together with a display device 2.

Hereinafter, embodiments of the invention will be described with reference to the drawings. FIG. 1 is a perspective view illustrating an imaging apparatus 1 provided with a region of interest tracing apparatus according to the invention, together with a display device 2.

The display device 2 has a configuration in which a display unit 52 including a large liquid crystal display device or the like is supported by a support mechanism 51.

The imaging apparatus 1 irradiates indocyanine green as a fluorescent dye injected into the body of a subject with excitation ray to photograph the fluorescence emitted from the indocyanine green, and displays the fluorescence image on the display device 2, together with a color image which is a visible image of the subject. In particular, the imaging apparatus 1 measures the intensity of fluorescence in the region of interest of the subject over time, together with the display of the fluorescence image and the color image described above, thereby obtaining a time intensity curve (TIC) of fluorescence in the region of interest of the subject.

The imaging apparatus 1 is equipped with a carriage 11 having four wheels 13, an arm mechanism 30 disposed in the vicinity of the front in a advancing direction of the carriage 11 on the upper surface of the carriage 11, a lighting and photographing unit 12 disposed on the arm mechanism 30 via a sub arm 41, and a monitor 15. A handle 14 used when moving the carriage 11 is attached to the rear of the carriage 11 in the advancing direction. Further, on the upper surface of the carriage 11, a recessed part 16 for mounting an operation portion (not illustrated) used for remote control of the imaging apparatus 1 is formed.

The aforementioned arm mechanism 30 is disposed on the front side of the carriage 11 in the advancing direction. The arm mechanism 30 includes a first arm member 31 connected to a support portion 37 disposed on a support column 36 erected on the front side in the advancing direction of the carriage 11 by a hinge portion 33. The first arm member 31 can swing with respect to the carriage 11 via the support column 36 and the support portion 37 by the action of the hinge portion 33. The above-described monitor 15 is attached to the support column 36.

A second arm member 32 is connected to the upper end of the first arm member 31 by the hinge portion 34. The second arm member 32 can swing with respect to the first arm member 31 by the action of the hinge portion 34. For this reason, the first arm member 31 and the second arm member 32 can take a photographing posture in which the first arm member 31 and the second arm member 32 illustrated in FIG. 1 are opened at a predetermined angle around the hinge portion 34 serving as a connecting portion between the first arm member 31 and the second arm member 32, and a standby posture in which the first arm member 31 and the second arm member 32 are close to each other.

The support portion 43 is connected to the lower end of the second arm member 32 by the hinge portion 35. The support portion 43 can swing with respect to the second arm member 32 by the action of the hinge portion 35. A rotating shaft 42 is supported by the support portion 43. Further, the sub arm 41 supporting the lighting and photographing unit 12 rotates about the rotating shaft 42 disposed at the distal end of the second arm member 32. For this reason, the lighting and photographing unit 12 moves between a position on the front side in the advancing direction of the carriage 11 with respect to the arm mechanism 30 for taking the photographing posture or the standby posture illustrated in FIG. 1 and a position on the rear side in the advancing direction of the carriage 11 with respect to the arm mechanism 30, which is the posture when the carriage 11 is moved, by the rotation of the sub arm 41.

Figure 2:
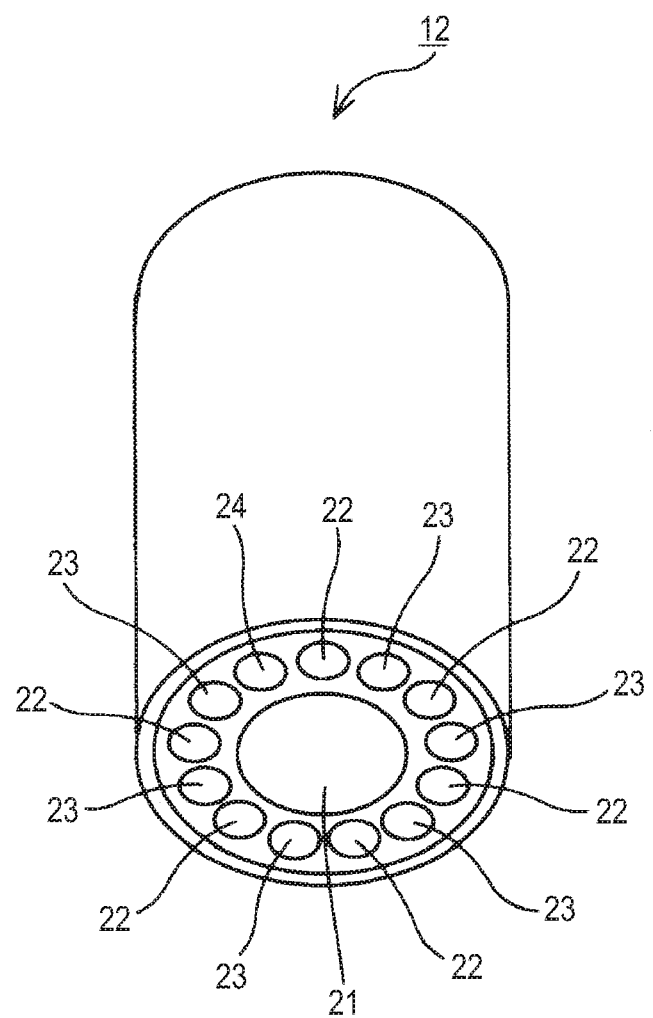
FIG. 2 is a schematic view of a lighting and photographing unit 12.

FIG. 2 is a schematic view of the lighting and photographing unit 12.

The lighting and photographing unit 12 includes a camera 21 having a plurality of image pickup elements capable of detecting near-infrared rays and visible rays, which will be described later, a visible ray source 22 made up of six LEDs disposed on the outer periphery of the camera 21, an excitation ray source 23 made up of six LEDs, and a checking ray source 24 made up of one LED. The visible ray source 22 emits visible rays. The excitation ray source 23 emits near-infrared rays having a wavelength of 760 nm, which is excitation ray for exciting indocyanine green. Further, the checking ray source 24 emits near-infrared rays having a wavelength of 810 nm which approximates the wavelength of fluorescence generated from indocyanine green. The wavelength of the excitation ray source 23 is not limited to 760 nm and may be a wavelength capable of exciting the indocyanine green. The wavelength of the checking ray source 24 is not limited to 810 nm and may be equal to or greater than the wavelength emitted from the indocyanine green.

Figure 3:
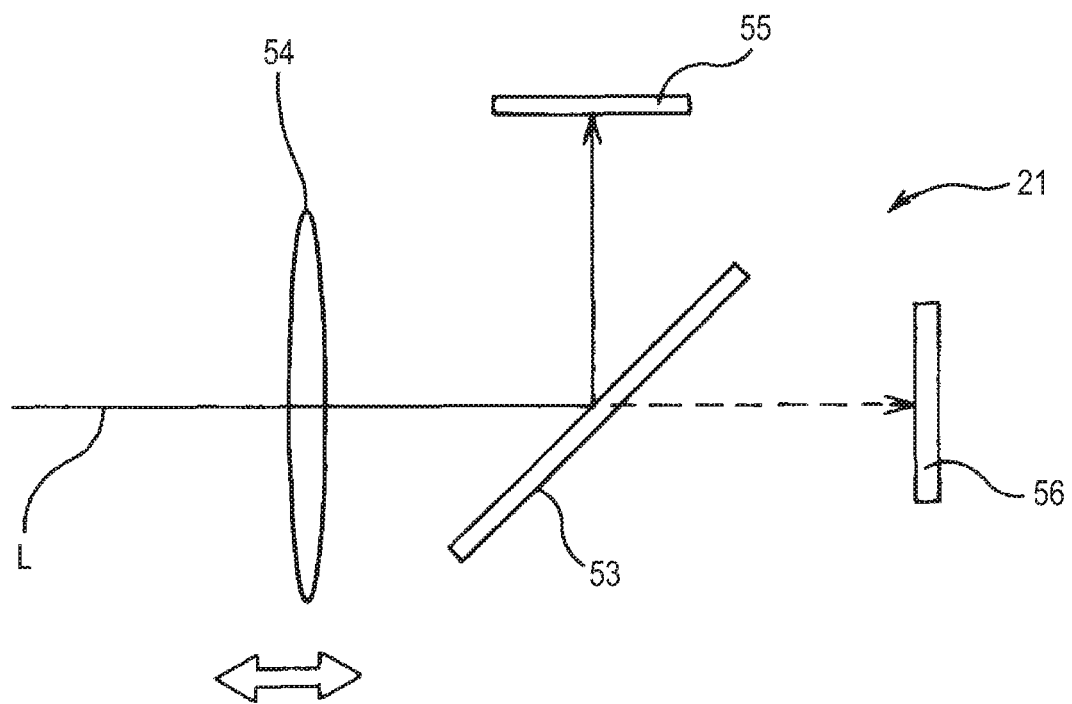
FIG. 3 is a schematic view of a camera 21 in a lighting and photographing unit 12.

FIG. 3 is a schematic view of the camera 21 in the lighting and photographing unit 12.

The camera 21 includes a movable lens 54 that reciprocates for focusing, a wavelength selection filter 53, a visible ray image pickup element 55, and a fluorescence image pickup element 56. The visible ray image pickup element 55 and the fluorescence image pickup element 56 are made up of a CMOS or a CCD. Further, as the visible ray image pickup element 55, an element capable of photographing an image of visible rays as a color image is used.

Visible rays and fluorescence coaxially incident on the camera 21 along its optical axis L pass through the movable lens 54 constituting the focusing mechanism and then reach the wavelength selection filter 53. Among visible rays and fluorescence incident coaxially, visible rays are reflected by the wavelength selection filter 53 and are incident on the visible ray image pickup element 55. Among visible rays and fluorescence coaxially incident, the fluorescence passes through the wavelength selection filter 53 and is incident on the fluorescence image pickup element 56. At this time, by the action of the focusing mechanism including the movable lens 54, the visible rays are focused on the visible ray image pickup element 55, and the fluorescence is focused on the fluorescence image pickup element 56. The visible ray image pickup element 55 photographs the visible image as a color image at a predetermined frame rate. Further, the fluorescence image pickup element 56 photographs a fluorescent image which is a near-infrared image at a predetermined frame rate.

Figure 4:
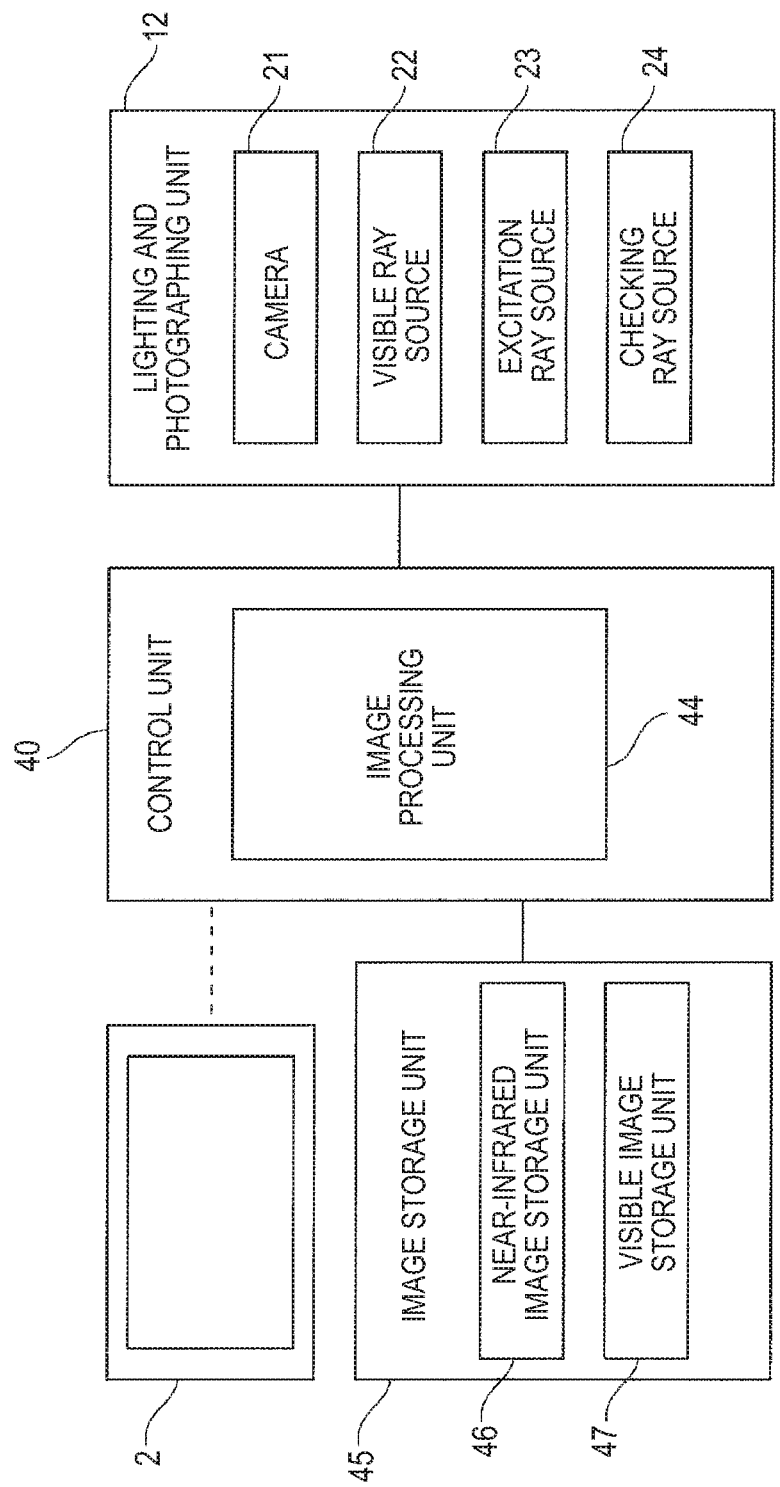
FIG. 4 is a block diagram illustrating a main control system of the imaging apparatus 1 according to the invention together with the display device 2.

FIG. 4 is a block diagram illustrating a main control system of the imaging apparatus 1 according to the invention, together with the display device 2.

The imaging apparatus 1 includes a CPU that executes a logical operation, a ROM that stores an operation program necessary for controlling the apparatus, a RAM that temporarily stores data and the like at the time of control, and the like, and includes a control unit 40 that controls the entire apparatus. The control unit 40 includes an image processing unit 44 that executes various kinds of image processes to be described later. The control unit 40 is connected to the above-described display device 2. The control unit 40 is also connected to the lighting and photographing unit 12 which includes a camera 21, a visible ray source 22, an excitation ray source 23, and a checking ray source 24. Further, the control unit 40 is connected to an image storage unit 45 that stores an image photographed by the camera 21. The image storage unit 45 includes a near-infrared image storage unit 46 which stores a near-infrared image, and a visible image storage unit 47 which stores a visible image (color image).

Figure 5:
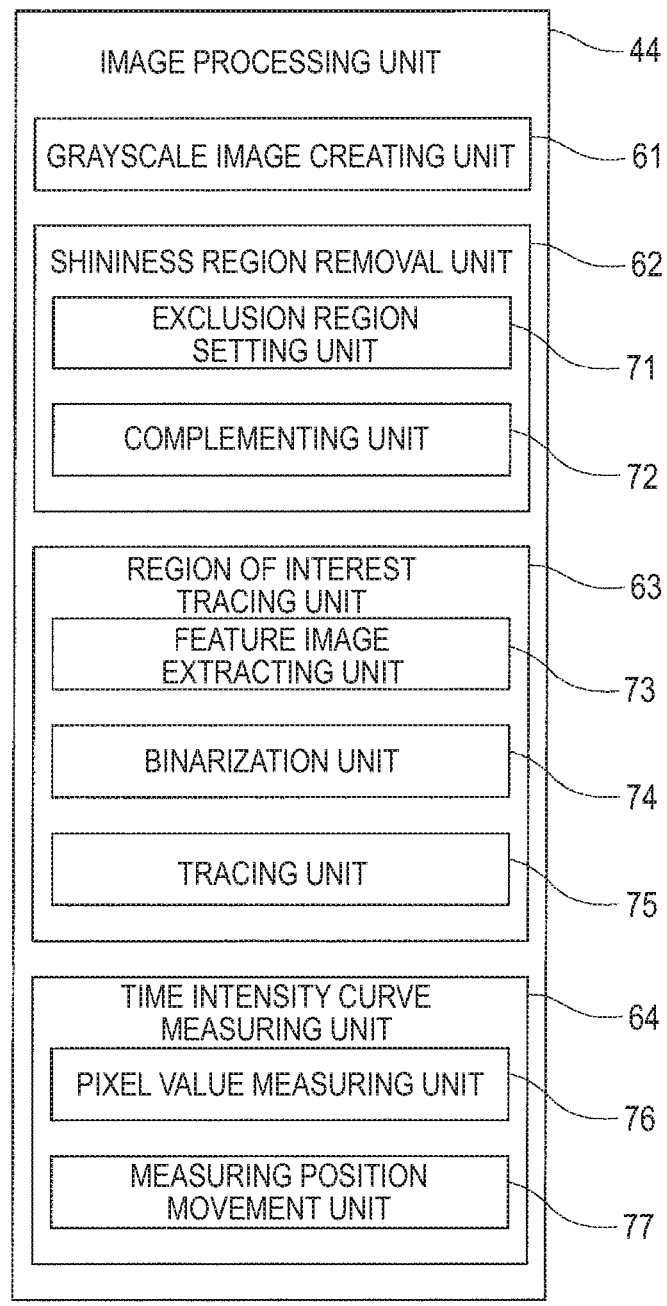
FIG. 5 is a block diagram of an image processing unit 44 in the control unit 40.

FIG. 5 is a block diagram of the image processing unit 44 in the control unit 40.

The image processing unit 44 includes a grayscale image creating unit 61, a shininess region removal unit 62, a region of interest tracing unit 63, and a time intensity curve measuring unit 64.

The above-described grayscale image creating unit 61 creates a grayscale image on the basis of the color image photographed by the visible ray image pickup element 55. Further, the shininess region removal unit 62 includes an exclusion region setting unit 71 which sets an exclusion region larger than the shininess region by adding a region in which the pixel value in the grayscale image created by the grayscale image creating unit 61 is larger than the threshold value and an outer peripheral region of the region in which the pixel value is larger than the threshold value, and a complementing unit 72 which complements pixels of the exclusion region on the basis of pixels on the outer peripheral portion of the exclusion region after the exclusion region is excluded from the color image. Further, the region of interest tracing unit 63 includes a feature image extracting unit 73 which extracts a feature image in the tissue on the basis of the grayscale image created by the grayscale image creating unit 61, a binarizing unit 74 which binarizes the grayscale image to create a binarized image, and a tracing unit 75 which traces the region of interest by detecting the amount of movement of the feature image in the binarized image created by the binarizing unit 74 over a plurality of frames. Further, the time intensity curve measuring unit 64 further includes a pixel value measuring unit 76 which measures a pixel value of a specific point in the fluorescence image photographed by the fluorescence image pickup element 56, and a measurement position movement unit 77 which moves the measured position of the pixel value in the pixel value measuring unit 76 in association with the region of interest traced by the region of interest tracing unit 63 described above.

When conducting surgery on a subject using the imaging apparatus 1 having the above-described configuration, first, the checking ray source 24 in the lighting and photographing unit 12 is turned on and the image of the irradiation region is photographed by the camera 21. Near-infrared rays having a wavelength of 810 nm which is close to the wavelength of fluorescence generated from indocyanine green is emitted from the checking ray source 24. The near-infrared rays cannot be checked by human eyes. On the other hand, when near-infrared rays having a wavelength of 810 nm are emitted from the checking ray source 24 and an image of this irradiation region is photographed by the camera 21, in a case where the camera 21 is operating normally, the image of the region to which the near-infrared rays are emitted is photographed by the camera 21, and the image is displayed on the display unit 52 of the display device 2. This makes it possible to easily check the operation of the camera 21.

Thereafter, indocyanine green is injected into the subject by injection. Further, near-infrared rays are emitted from the excitation ray source 23 in the lighting and photographing unit 12 toward the affected part in the tissue of the subject, and the visible rays are emitted from the visible ray source 22. As the near-infrared rays emitted from the excitation ray source 23, as described above, near-infrared rays of 760 nm, which act as excitation rays for indocyanine green to emit fluorescence, are adopted. As a result, indocyanine green injected into the subject's body generates fluorescence in the near-infrared region with a peak at about 800 nm.

Further, the vicinity of the affected part in the tissue of the subject is photographed at the predetermined frame rate by the camera 21 in the lighting and photographing unit 12. As described above, the camera 21 can detect near-infrared rays and visible rays. The near-infrared image and the color image photographed at the predetermined frame rate by the camera 21 are converted into the image data capable of displaying the near-infrared image and the color image on the display unit 52 of the display device 2 by the image processing unit 44, and are displayed on the display unit 52. Further, if necessary, the image processing unit 44 creates a synthetic image obtained by combining the color image and the near-infrared image using the near-infrared image data and the color image data. Further, the near-infrared image and the color image photographed by the camera 21 are stored in the near-infrared image storage unit 46 and the visible image storage unit 47 in the image storage unit 45 as needed.

In such an imaging apparatus 1, a color image of an affected part in a tissue of a subject and a near-infrared image are simultaneously stored as a moving image, and a photographed image recorded by a video recorder is reproduced as a moving image. That is, in such an imaging apparatus 1, by recording and reproducing an image photographed at a predetermined frame rate as a moving image, it is possible to observe driving of a blood vessel and lymph duct after administration of a fluorescent dye such as ICG under a bright external lighting environment and to check the region of the cancer lesion. Such recorded data can be used not only for reference, but also new knowledge can be obtained by utilizing the recorded data for analysis. That is, in the analysis of the time intensity curve (TIC) for drawing the signal change curve of the time-direction of the region of interest, by obtaining the time until the pixel value of the near-infrared image in the region of interest becomes a peak, it is possible to quantitatively evaluate the contrast time of the fluorescent dye such as indocyanine green.

In order to obtain such a time intensity curve, it is necessary to set the region of the blood vessel of the subject as a region of interest and to measure the pixel value of the near-infrared image of the region of interest over time. On the other hand, the region of interest of the subject moves due to body movement etc. of the subject. Therefore, in the imaging apparatus 1, a configuration is adopted in which an accurate time intensity curve is measured by tracing the region of interest, irrespective of the movement of the region of interest. That is, in the imaging apparatus 1, after the shininess region is removed from the color image including the tissue of the subject, by tracing the region of interest using the color image, the pixel value of the same position is always measured.

Hereinafter, an operation for obtaining a time intensity curve using the imaging apparatus 1 will be described. FIGS. 6 to 10 are schematic views illustrating the transition of the image including the region of interest of the subject obtained by the image processing unit 44 in the imaging apparatus 1 according to the invention. In these drawings, the transition of the image in the vicinity of the heart of the subject is schematically illustrated.

<Shininess Removal>

Figure 6:
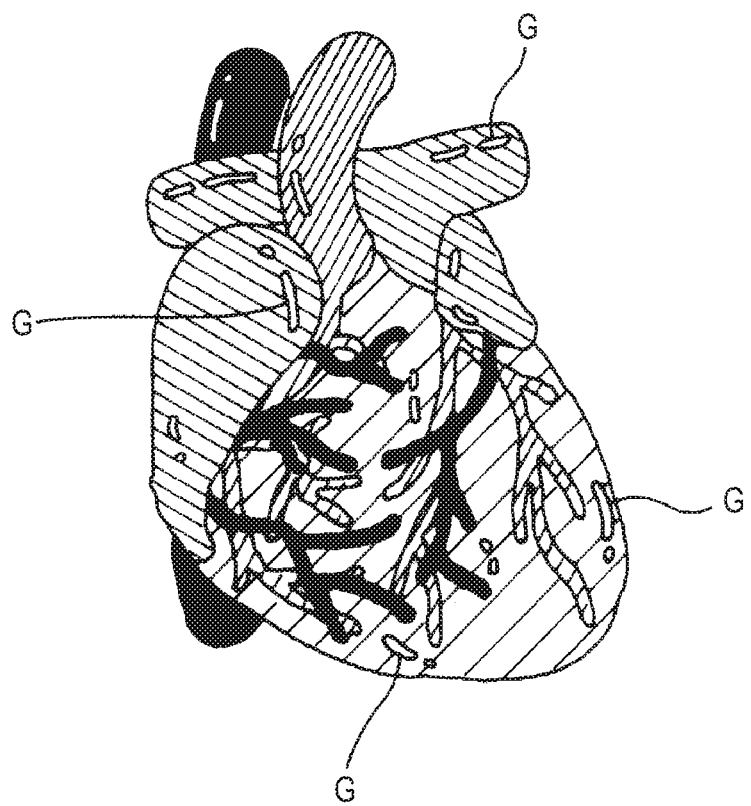
FIG. 6 is a schematic view illustrating a transition of the image including the region of interest of the subject obtained by the image processing unit 44.

Among these drawings, FIG. 6 schematically illustrates a color image of the tissue of the subject photographed by the visible ray image pickup element 55. The tissue of the subject when performing the surgery is in a situation in which shininess is likely to occur due to body fluids or fluids such as physiological saline used at the time of surgery. On the other hand, the lighting and photographing unit 12 often photographs a color image by emitting visible rays from directly above the subject, and the irradiation direction of the visible rays emitted by the visible ray source 22 and the photographing direction of the color image provided by the visible ray image pickup element 55 coincide with each other. Therefore, in the color image obtained by photographing the tissue of the subject, a shininess region G is generated. In FIG. 6, the shininess region G is illustrated as an outlined blank region. In FIG. 6, the symbol G is attached only to a partial shininess region among a plurality of shininess regions. Here, the shininess region means a region in which a part of the tissue looks shiny as compared with other regions due to the presence of the liquid.

The region of interest in the color image coincides with the region of interest in which the doctor examines in the surgical field. For this reason, a shininess region which is not seen in the visual field of the doctor is displayed on the color image. Therefore, the color image and the visual field of the doctor are different from each other. Further, when the shininess region exists in the color image, various image processes such as edge emphasis and feature image extraction are hindered.

Therefore, in the imaging apparatus 1, first, the shininess removal process on the color image is executed by the shininess region removal unit 62 in the image processing unit 44. In the shininess removal process using the shininess region removal unit 62, the grayscale image created from the color image by the grayscale image creating unit 61 is used. Further, by the exclusion region setting unit 71, a region in which the pixel value in the grayscale image is larger than the threshold value and the outer peripheral region of the region in which the pixel value is larger than the threshold value are added, and an exclusion region larger than the shininess region is set. Thereafter, after the exclusion region is excluded from the color image by the complementing unit 72, the pixels in the exclusion region are complemented on the basis of the pixels on the outer peripheral portion of the exclusion region.

Figure 11:
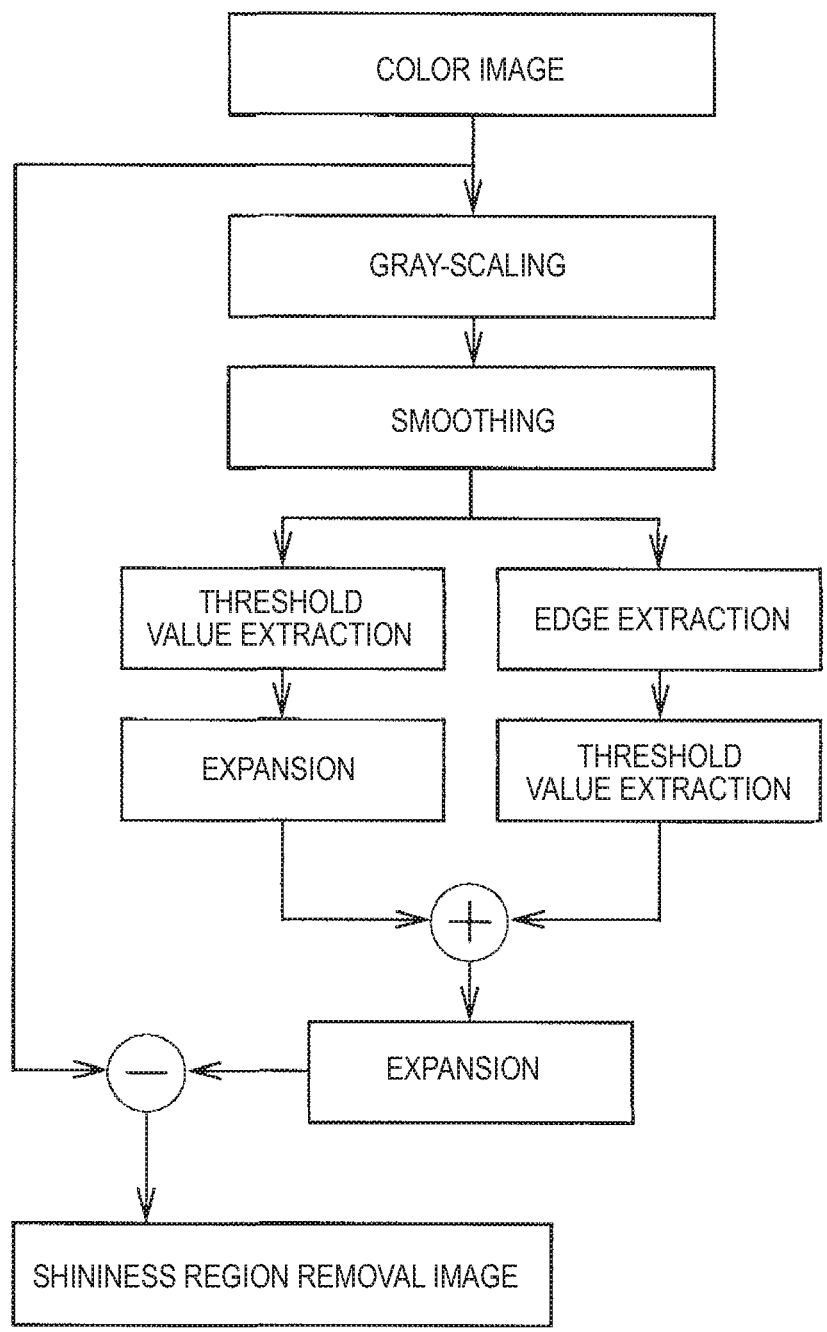
FIG. 11 is a block diagram illustrating a flow of a shininess removal process.

Hereinafter, the shininess removal process will be described in detail. FIG. 11 is a block diagram illustrating the flow of the shininess removal process. Further, FIGS. 12 to 17 are schematic views conceptually illustrating pixel values and sizes of regions extracted from the shininess region. Further, FIGS. 18 to 22 are schematic views conceptually illustrating a region extracted from the shininess region. In FIGS. 12 to 17, a vertical axis indicates pixel values and a horizontal axis indicates positions.

When performing the shininess removal process, first, by the grayscale image creating unit 61 illustrated in FIG. 5, the color image photographed by the visible ray image pickup element 55 is converted into grayscale. When converting the color image into grayscale, general methods such as BT. 601, BT. 709, R value extraction, G value extraction, B value extraction, RB value average, RG value average, GB value average, RGB value average, MAX value, MIN value, MAX·MIN average value, MAX-MIN value, 255× (MAX− MIN)/MAX value, and an intermediate value of RGB may be used.

Figure 12:
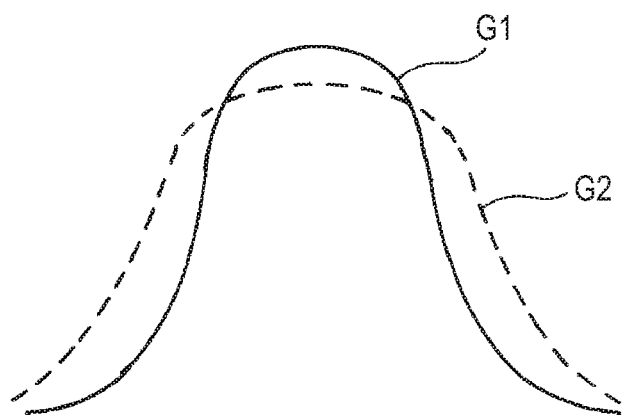
FIG. 12 is a schematic view conceptually illustrating a pixel value and a size of a region extracted from a shininess region.

Further, a smoothing process is performed on the grayscale image. FIG. 12 illustrates pixel values and sizes of regions extracted from the shininess region before and after the smoothing process. In FIG. 12, G1 indicates the pixel value and size of the region extracted from the shininess region before the smoothing process, and G2 indicates the pixel value and size of the region extracted from the shininess region after the smoothing process. By the smoothing process, noise in the grayscale image can be removed.

Figure 13:
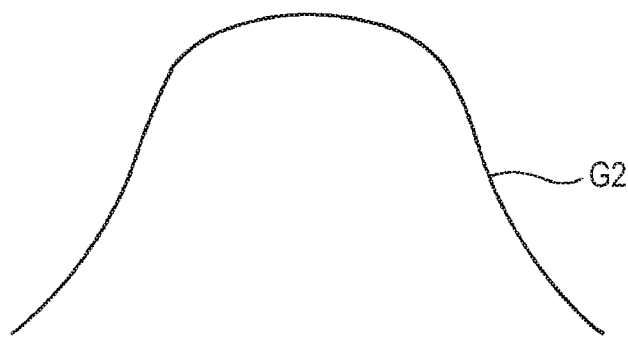
FIG. 13 is a schematic view conceptually illustrating a pixel value and a size of the region extracted from the shininess region.
Figure 14:
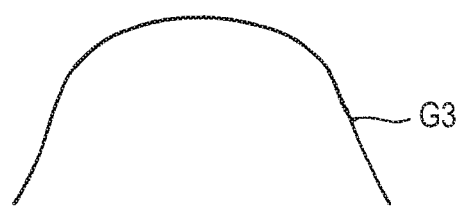
FIG. 14 is a schematic view conceptually illustrating a pixel value and a size of a region extracted from the shininess region.
Figure 15:
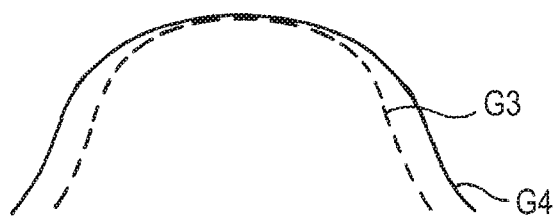
FIG. 15 is a schematic view conceptually illustrating a pixel value and a size of the region extracted from the shininess region.
Figure 18:
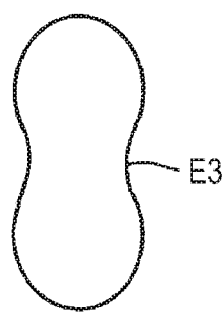
FIG. 18 is a schematic view conceptually illustrating a region extracted from the shininess region.
Figure 19:
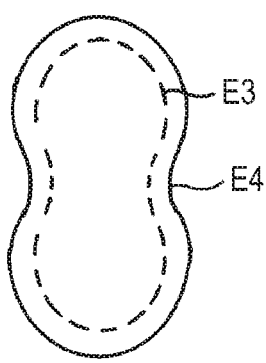
FIG. 19 is a schematic view conceptually illustrating the region extracted from the shininess region.

Next, a threshold value is extracted for the image after the smoothing process. The extraction of the threshold value is performed by subtracting the pixel value corresponding to the threshold value from each pixel value in the grayscale image. G2 in FIG. 13 illustrates the pixel value and size of the region extracted from the shininess region before the threshold value extraction, and G3 in FIG. illustrates the pixel value and size of the region extracted from the shininess region after the threshold value extraction. Thereafter, an expanding process is performed on the image after the threshold value extraction. G3 in FIG. 15 illustrates the pixel value and the size of the region extracted from the shininess region before the expanding process, G4 in FIG. 15 illustrates the pixel value and the size of the region extracted from the shininess region after the expanding process. E3 in FIGS. 18 and 19 illustrates a region extracted from the shininess region before the expanding process, and E4 in FIG. 19 illustrates a region extracted from the shininess region after the expanding process.

Figure 16:
FIG. 16 is a schematic view conceptually illustrating a pixel value and a size of a region extracted from a shininess region.
Figure 17:
FIG. 17 is a schematic view conceptually illustrating a pixel value and a size of a region extracted from a shininess region.
Figure 20:
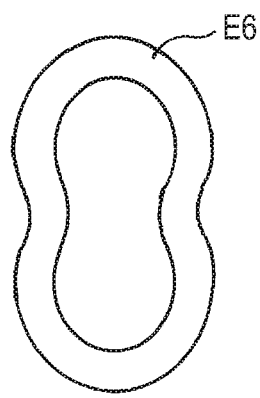
FIG. 20 is a schematic view conceptually illustrating the region extracted from the shininess region.

Also, as illustrated in FIG. 11, an edge extraction process is performed on the image after the smoothing process in parallel with this. In the edge extraction process, for example, 3×3 Mean Filter process is applied to the image after smoothing process twice in succession, and the second process result is subtracted from the first process result. G5 in FIG. 16 illustrates the pixel value and the size of the region extracted from the shininess region after the edge extraction process. The pixel value and the size of the region extracted from the shininess region are changed from the state illustrated in FIG. 13 to the state illustrated in FIG. 16. Further, a threshold value is extracted for the image after the edge extraction process. The extraction of the threshold value is performed by subtracting the pixel value corresponding to the threshold value from each pixel value in the grayscale image. G6 in FIG. 17 illustrates the pixel value and the size of the region extracted from the shininess region after the threshold value extraction. Further, E6 in FIG. 20 illustrates a substantially doughnut-shaped region formed with a blank region in the center part and extracted from the shininess region after the threshold value is extracted.

Figure 21:
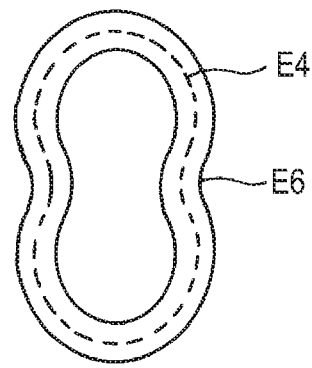
FIG. 21 is a schematic view conceptually illustrating the region extracted from the shininess region.

Thereafter, the image after the threshold value is extracted and the expanding process is performed and the image subjected to the threshold value extraction after the edge extraction are added. That is, the image after the threshold value is extracted and the expanding process is performed and the image subjected to the threshold value extraction after the edge extraction are combined into one image. FIG. 21 illustrates a state in which the region E4 and the region E6 are added. As illustrated in the drawings, the blank region at the central part of the region E6 is filled with the region E4.

Figure 22:
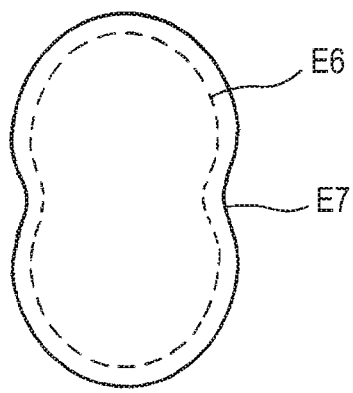
FIG. 22 is a schematic view conceptually illustrating the region extracted from the shininess region.

Thereafter, an expanding process is executed on the image after the addition. In FIG. 22, a region E7 expanded from the region E6 illustrated in FIG. 21 is illustrated. The region E7 is a region larger than the shininess region G illustrated in FIG. 7. Further, as illustrated in FIG. 11, this region is set as the extraction region, and is excluded by being subtracted from the original color image.

Figure 7:
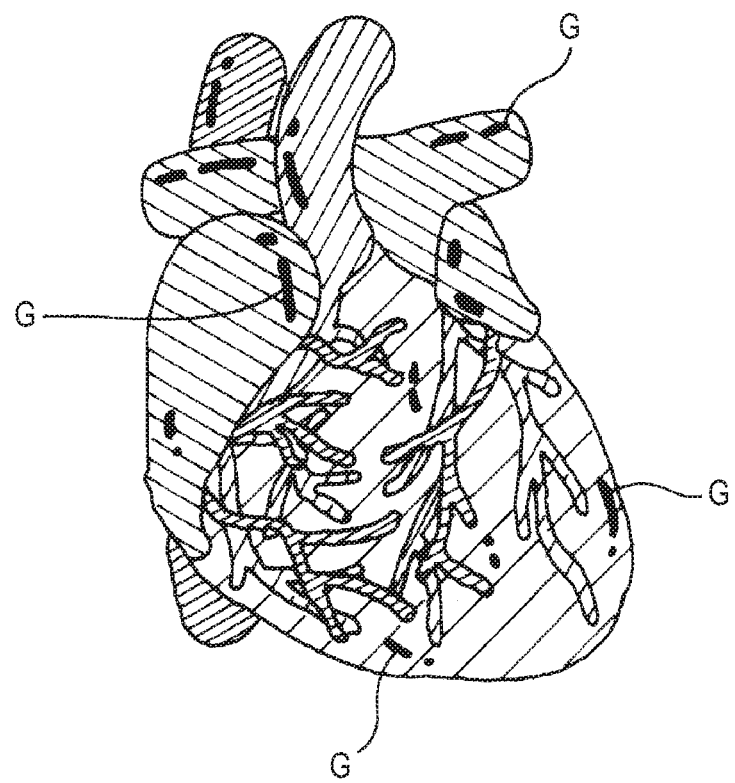
FIG. 7 is a schematic view illustrating a transition of the image including the region of interest of the subject obtained by the image processing unit 44.

FIG. 7 schematically illustrates a state in which an exclusion region, which is a region larger than the shininess region, is excluded from the color image of the tissue of the subject photographed by the visible ray image pickup element 55. In FIG. 7, the excluded region is illustrated as a blackened region. In FIG. 7, the same reference sign G as the shininess region is added to the excluded region. In FIG. 7, the reference sign G is attached only to a partial exclusion region among the plurality of exclusion regions.

After the exclusion region larger than the shininess region is excluded from the color image of the tissue of the subject, pixels of the exclusion region are complemented on the basis of the pixels of the outer peripheral part of the exclusion region. The complementation can be carried out, for example, by a contour tracing method.

Figure 23:
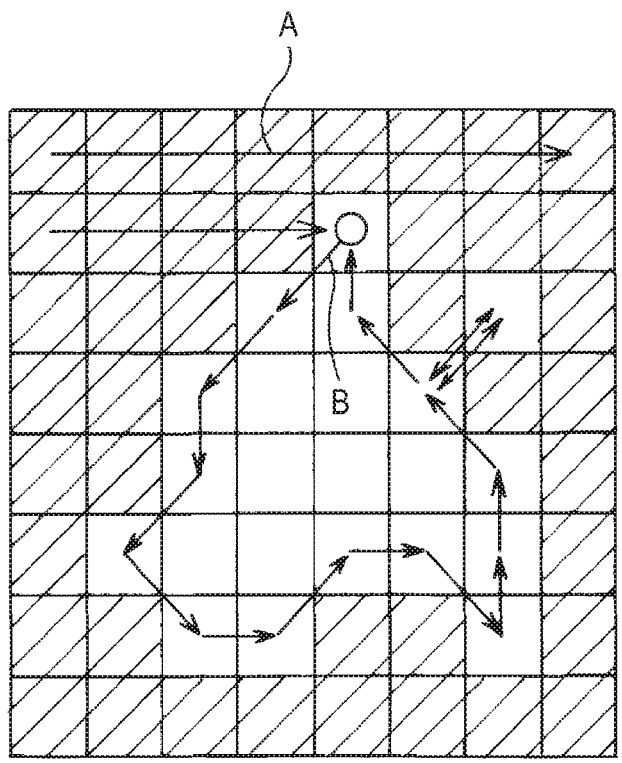
FIG. 23 is an explanatory view schematically illustrating a process of complementing pixels in an exclusion region on the basis of pixels on an outer peripheral portion of the exclusion region by a contour tracing method.

FIG. 23 is an explanatory diagram schematically illustrating a process of complementing pixels of the exclusion region on the basis of the pixels on the outer peripheral part of the exclusion region by the contour tracing method. In FIG. 23, the regions requiring complementation, that is, the above-described exclusion regions are represented by blank regions, and other regions are hatched.

The contour tracing method is a method in which a predetermined region in an image is scanned as indicated by an arrow A, and as illustrated by an arrow B, while tracing the region requiring the complementation, that is, the contour of the above-mentioned exclusion region, complementation is performed from the periphery toward the central part. For each region that needs to be complemented, complementation is performed using the average value of pixels neighboring a pixel in question or the median value. Here, the pixels neighboring the pixel in question are, for example, two left and right pixels with respect to the pixel in question, two upper and lower pixels with respect to the pixel in question, or eight pixels neighboring the pixel in question. In FIG. 23, although the contour is two-dimensionally traced and complemented, the contour may be traced and complemented by one line.

In addition, the complementation may be performed by the image reduction method instead of the above-described contour tracing method. The image reduction method is a method in which, by reducing the entire image by one pixel in the upper and lower and right and left directions at the center of the region requiring complementation, appearance of colors at the same coordinates as the outline portion is used and complementation is performed with that color. The logic at the time of reduction may be linear, bi-cubic, or any other.

Further, complementation may be performed by a linear approximation and ambient correction method, instead of the above-described contour tracing method. The linear approximation and ambient correction method is a method of focusing on one line and performing the linear complementation, using the colors of the starting point and the ending point pixel which are away from the outline by one pixel. After the linear complementation is performed, if color exists on the adjacent lines, the ambient correction that adopts the average value with them is executed.

Figure 8:
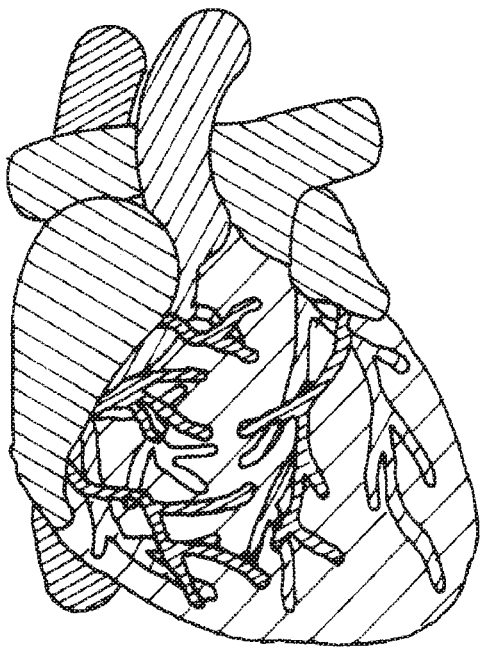
FIG. 8 is a schematic view illustrating a transition of the image including the region of interest of the subject obtained by the image processing unit 44.

FIG. 8 schematically illustrates a state after the above-described shininess removal is performed on the color image of the tissue of the subject. By executing the above described shininess removal, it is possible to remove the shininess region from the color image of the subject's tissue without discomfort.

<Region of Interest Tracing>

Upon completion of the above-described shininess removal process, next, a region of interest tracing process of tracing a region of interest in the tissue on the basis of the color image including the tissue of the subject is executed. The region of interest tracing process is mainly executed by the region of interest tracing unit 63 illustrated in FIG. 5.

Figure 9:
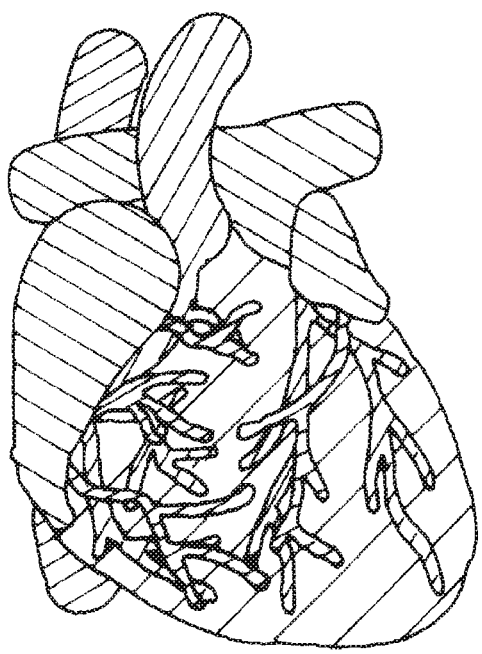
FIG. 9 is a schematic view illustrating a transition of the image including the region of interest of the subject obtained by the image processing unit 44.

At this time, first, a color image from which the shininess region is removed by the above-described shininess removal process is gray-scaled to create a grayscale image. The creation of the grayscale image is executed by the grayscale image creating unit 61 illustrated in FIG. 5. The gray-scaling of the color image may be performed, using general methods such as BT. 601, BT. 709, R value extraction, G value extraction, B value extraction, RB value average, RG value average, GB value average, RGB value average, MAX value, MIN value, MAX·MIN average value, MAX−MIN value, 255×(MAX−MIN)/MAX value, intermediate value of RGB, similarly to the aforementioned shininess removal process. FIG. 9 schematically illustrates the grayscale image of the tissue of the subject created in this way.

Next, a feature image is created from the grayscale image by the feature image extracting unit 73 illustrated in FIG. 5. The feature image is an image obtained by extracting blood vessels and wrinkles of the subject as feature quantities. For extraction of the feature image, various methods such as a simple convolution, a Laplacian filter, an unsharp mask, a method using an energy function, and the like can be used for feature extraction. At this time, in order to execute the real-time processing, it is preferable to use convolution, Laplacian filter, unsharp mask or the like.

A case where an unsharp mask is used for extracting this feature image will be described. In the case of using the unsharp mask, when the blurring coefficient is set as 's' and the weight is set as 'w' (0<w<1), the grayscale image is blurred by applying an average of s×s or a Gaussian filter, thereby creating a blurred image. Then, an output image obtained by extracting a feature image by the following equation is computed.

$$\text{Output image} = (\text{original image} - w \times \text{blurred image})/(1-w)$$

Figure 10:
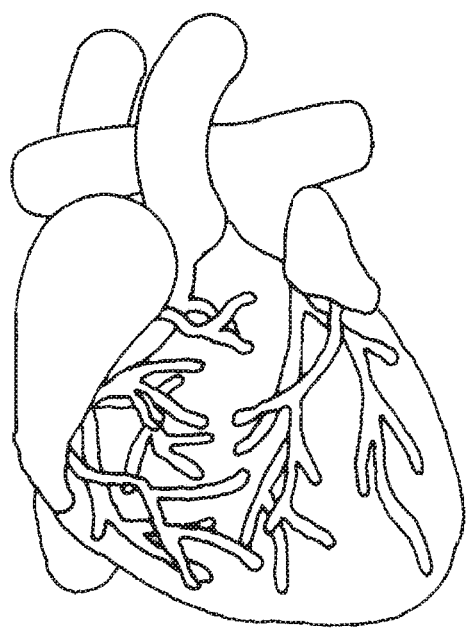
FIG. 10 is a schematic view illustrating a transition of the image including the region of interest of the subject obtained by the image processing unit 44.

After the extraction of the feature image, the binarization process is executed by the binarizing unit 74 illustrated in FIG. 5. In FIG. 10, the output image after the feature image is extracted and binarized is schematically illustrated. In FIG. 10, feature images that are normally displayed brighter are represented by lines.

Next, by the tracing unit 75 illustrated in FIG. 5, the region of interest is traced, by detecting the amount of movement of the feature image over a plurality of frames, using the feature image after binarization. Tracing of this region of interest can be carried out using, for example, a movement vector calculation method or a pattern matching method.

Figure 24:
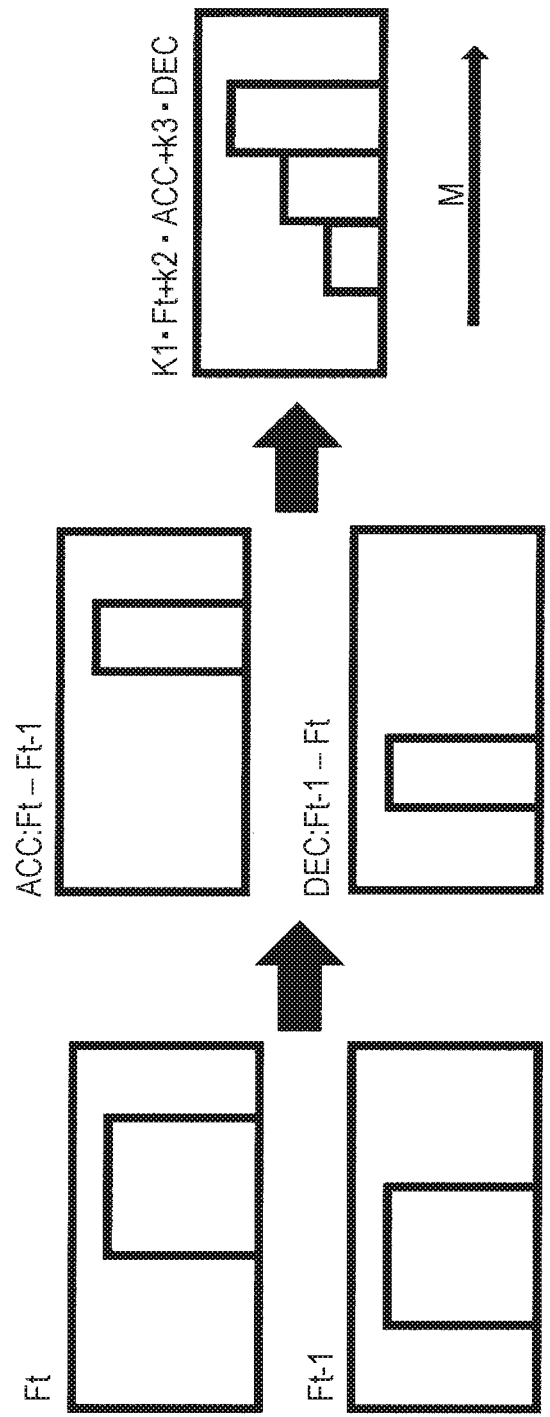
FIG. 24 is an explanatory view schematically illustrating an operation of detecting an amount of movement of a feature image over a plurality of frames by a movement vector calculation method.

FIG. 24 is an explanatory diagram schematically illustrating an operation of detecting an amount of movement of a feature image over a plurality of frames by a movement vector calculation method. The horizontal axis of the rectangular region in the drawing illustrates the position and the vertical axis illustrates the pixel value.

In the drawing, Ft on the left side of the drawing illustrates the current frame of the feature image, and Ft-1 illustrates the past frame (previous frame) of the feature image. The middle ACC in the drawing illustrates the result obtained by subtracting the past frame from the current frame of the feature image, and DEC illustrates the result obtained by subtracting the current frame from the past frame of the feature image. The right side of the drawing illustrates the calculation result of the following formula when k1, k2, and k3 are set as arbitrary coefficients (here, k1>k2>k3).

$$k1 \cdot Ft + k2 \cdot ACC + k3 \cdot DEC$$

In FIG. 24, as illustrated on the right side of the drawing, the pixel value of the difference image after the calculation increases toward the right side. For example, when k1=2, k2=1, and k3=−1 and the maximum value of the binarized image is 1, the background of the image is 0, the disappearing pixel in which the image moved to background is 1, the unchanged pixel is 2, the newly appearing image is 3, and the pixel value of the difference image increases to 1, 2, and 3 toward the right side. As a result, as illustrated by an arrow M on the right side in the drawing, it can be recognized that this image moves to the right side with the lapse of time. Such a calculation is continuously executed over a plurality of frames. Further, by setting the pixels of the corner or the center of the region of interest as reference coordinates, it is possible to calculate the movement vector, for example, using the numbers and ratios of lost pixels and appearance pixels in the up, down, left and right directions of the reference coordinates, by using the above difference image.

Further, it is also possible to trace a region of interest, using a pattern matching method instead of the above-described movement vector calculation method. In this case, a pattern in which pixels of the N×N region among the region of interest are used as a template is adopted. M is an integer larger than N, and the pattern matching is performed on the M×M region among the regions including the region of interest. This pattern matching is performed by calculating a similarity degree, using a method such as a correlation function, variance, and standard deviation. With this pattern matching, it is possible to detect the amount of movement of the feature image over a plurality of frames.

In this manner, it is possible to trace the region of interest by detecting the amount of movement of the feature image over the entire region of the feature image. Therefore, movement of a specific position in the feature image can be traced over a plurality of frames.

<Time Intensity Curve Measurement>

Next, a time intensity curve measuring process of analyzing a time intensity curve for drawing a signal change curve in the time-direction of the intensity of the fluorescence of the region of interest by utilizing the tracing result of the region of interest described above will be described.

For the measurement of the time intensity curve, the above-described tracing result of the region of interest is used. That is, the time intensity curve measurement is performed, by moving the measurement position of the pixel value of the fluorescence image measured by the pixel value measuring unit 76 in the time intensity curve measuring unit 64 illustrated in FIG. 5 in association with the region of interest traced by the region of interest tracing unit 63, by the measurement position movement unit 77 in the time intensity curve measuring unit 64.

When analyzing the time intensity curve, a position at which the intensity of fluorescence from indocyanine green in the fluorescence image photographed by the fluorescence image pickup element 56 is measured over time is previously set as a measurement point. Further, the intensity of fluorescence at this measurement point is measured by the pixel value measuring unit 76. The position of this measurement point moves with body movement or the like of the subject. Therefore, by the measurement position movement unit 77, the measurement position of the pixel value in the pixel value measuring unit 76 is moved in association with the region of interest traced by the region of interest tracing unit 63 described above. By adopting such a configuration, even when the measurement point moves, the measurement point is traced and the measurement of the pixel value can be performed.

Figure 25:
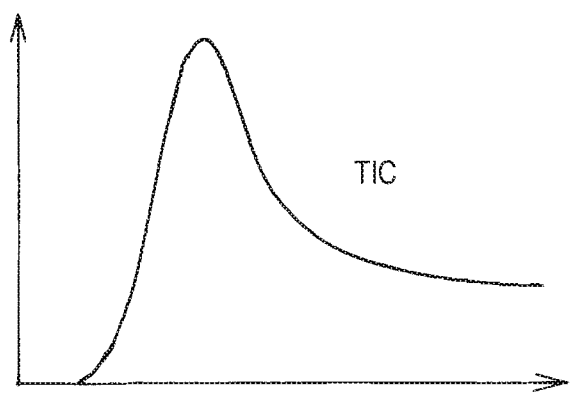
FIG. 25 is a graph illustrating a time intensity curve (TIC).

FIG. 25 is a graph illustrating the time intensity curve (TIC) measured in this way. In this drawing, the vertical axis illustrates the pixel value at the measurement point, that is, the intensity of fluorescence from indocyanine green, and the horizontal axis illustrates time.

In the TIC analysis, it is possible to quantitatively evaluate the contrast time of indocyanine green, by obtaining the time until the pixel value of the fluorescence from the indocyanine green in the region of interest becomes a peak. Further, in the imaging apparatus 1, the measurement position of the pixel value measured by the pixel value measuring unit 76 is moved by the measurement position movement unit 77 in association with the region of interest traced by the region of interest tracing unit 63. Therefore, even when the region of interest moves due to body movement or the like of the subject, it is possible to always measure the pixel value at a certain position, and it is possible to obtain an accurate time intensity curve.

Further, in the above-described embodiment, by recognizing the movement of the tissue in a large number of regions of the fluorescence image, and by measuring the time intensity curve in the regions to display the map, it is also possible to perform quantitative evaluation not only in the region of interest but also in the entire surgical field.

In the aforementioned embodiment, as the camera 21, a camera which separately includes the visible ray image pickup element 55 which captures a color image including the tissue of the subject and the fluorescence image pickup element 56 which photographs the fluorescence image from the indocyanine green has been described. However, a configuration in which a color image including the tissue of the subject and a fluorescence image from the indocyanine green are photographed by a single image pickup element or the like may be adopted.

The invention claimed is:

1. A time intensity curve measuring apparatus which measures a time intensity curve illustrating a temporal change in pixel value of light emission from a fluorescent dye administered into a body of a subject, the apparatus comprising:
   an excitation ray source which emits near-infrared rays for exciting a fluorescent dye administered into the body of the subject toward the subject;
   an image pickup unit including:
     a first photographing element configured to detect near-infrared rays from the fluorescent dye, and obtain a fluorescence image of a tissue of the subject; and
     a second photographing element configured to detect visible rays, and obtain a color image of the tissue of the subject; and
     a wavelength selection filter configured to make visible rays and fluorescence incident coaxially split into visible rays and fluorescence such that the fluorescence is incident on the first photographing element and the visible rays are incident on the second photographing element,
   the image pickup unit being configured to simultaneously detect near-infrared rays from the fluorescent dye and visible rays, and obtain a plurality of fluorescence images of the tissue of the subject and a plurality of color images of the tissue of the subject, wherein each of the plurality of fluorescence images is obtained by the first photographing element based on the detected near-infrared rays from the fluorescent dye and each of the plurality of color images is obtained by the second photographing element based on the detected visible rays, the plurality of fluorescence images include a first fluorescence image and a second fluorescence image, the plurality of color images include a first color image and a second color image, and the second fluorescence image and the second color image are taken simultaneously at a time later than and different from a time when the first fluorescence image and the first color image are taken simultaneously;
   a first region of interest setting unit which sets a region of interest at a position on the first fluorescence image;
   a tissue specifying unit which specifies a position of the tissue on the first color image, the position corresponding to the position of the region of interest on the first fluorescence image;
   a tissue tracing unit which creates a tissue image including the tissue based on at least one of the plurality of color images, and specifies a position of the tissue on the second color image based on the second color image and the tissue image, and calculates a vector of movement of the tissue between the first color image and the second color image based on the position of the tissue on the first color image and the position of the tissue on the second color image;
   a second region of interest setting unit which sets the region of interest at a position on the second fluorescence image, wherein the position is calculated based on the position of the region of interest on the first fluorescence image and the vector of movement of the tissue, and the position corresponds to the position of the tissue on the second color image; and
   a pixel value measuring unit which measures a pixel value of the region of interest.

2. The time intensity curve measuring apparatus according to claim 1, the time intensity curve measuring apparatus further comprising:
   a shininess region removal unit which removes a shininess region on a tissue surface on the basis of a color image including the tissue,
   wherein the tissue tracing unit traces the region of interest on the basis of the color image after the shininess region is removed by the shininess region removal unit.

3. The time intensity curve measuring apparatus according to claim 1, wherein the tissue tracing unit detects an amount of movement of the tissue image by a movement vector calculation method.

4. The time intensity curve measuring apparatus according to claim 1, wherein the tissue tracing unit detects an amount of movement of the tissue image by a pattern matching method.

* * * * *